United States Patent [19]

Keane

[11] Patent Number: 4,916,309

[45] Date of Patent: Apr. 10, 1990

[54] APPLIANCE FOR CONVERTING REFLECTANCE MEASURING INSTRUMENT INTO A TRANSMITTANCE MEASURING INSTRUMENT

[75] Inventor: Thomas J. Keane, Gaithersburg, Md.

[73] Assignee: BYK-Gardner, Inc., Silver Spring, Md.

[21] Appl. No.: 294,678

[22] Filed: Jan. 9, 1989

[51] Int. Cl.$^4$ ............................................. H01J 5/16
[52] U.S. Cl. ........................... 250/227.29; 350/96.1; 356/244; 356/432; 356/445
[58] Field of Search ................... 250/227, 216, 239; 350/96.1

[56] References Cited

U.S. PATENT DOCUMENTS

| | | | |
|---|---|---|---|
| 2,547,543 | 4/1951 | Strong | 88/14 |
| 3,936,189 | 2/1976 | DeRemigis | 356/73 |
| 3,998,551 | 12/1976 | Suga | 356/73 |
| 4,082,458 | 4/1978 | Fukui et al. | 356/73 |
| 4,120,582 | 10/1978 | De Vries et al. | 356/73 |
| 4,564,290 | 1/1986 | Bell et al. | 356/73 |
| 4,602,160 | 7/1986 | Mactaggart | 250/341 |
| 4,750,835 | 6/1988 | McMurtry | 250/227 |
| 4,808,812 | 2/1989 | Tanaka et al. | 250/216 |

Primary Examiner—David C. Nelms
Assistant Examiner—Khaled Shami
Attorney, Agent, or Firm—Leydig, Voit & Mayer

[57] ABSTRACT

An appliance for converting an optical reflectance measuring instrument into a transmittance measuring instrument is shaped to fit in the aperture of a probe of the reflectance measuring instrument. When used as a reflectance measuring instrument, reflectance samples are positioned over the aperture. The appliance has a fiber optic cable which receives light from the probe and carries it out through the aperture and redirects the light back toward the aperture through a position designed to receive a sample, the transmittance of which is to be measured. In the optical instrument, the light received by the probe is carried by fiber optics to a spectrometer.

4 Claims, 1 Drawing Sheet

U.S. Patent
Apr. 10, 1990
4,916,309
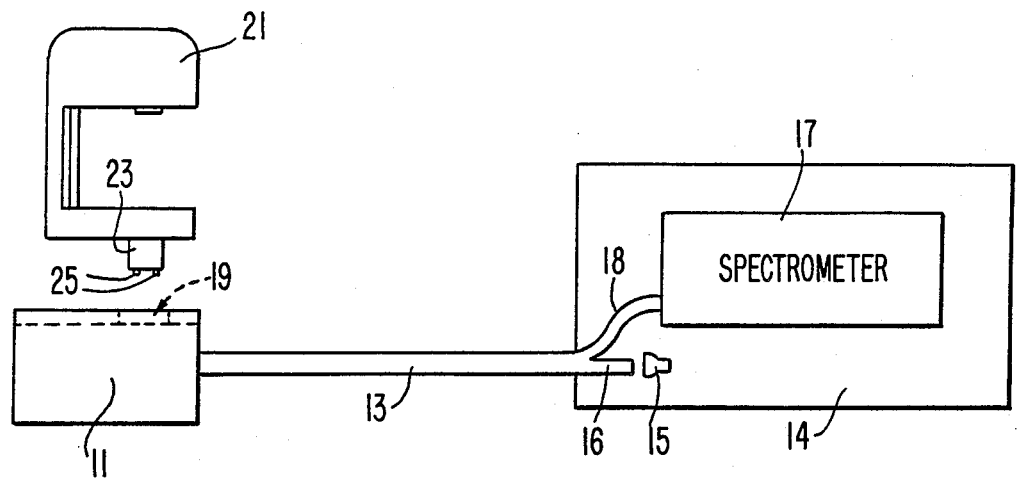
FIG. 1.
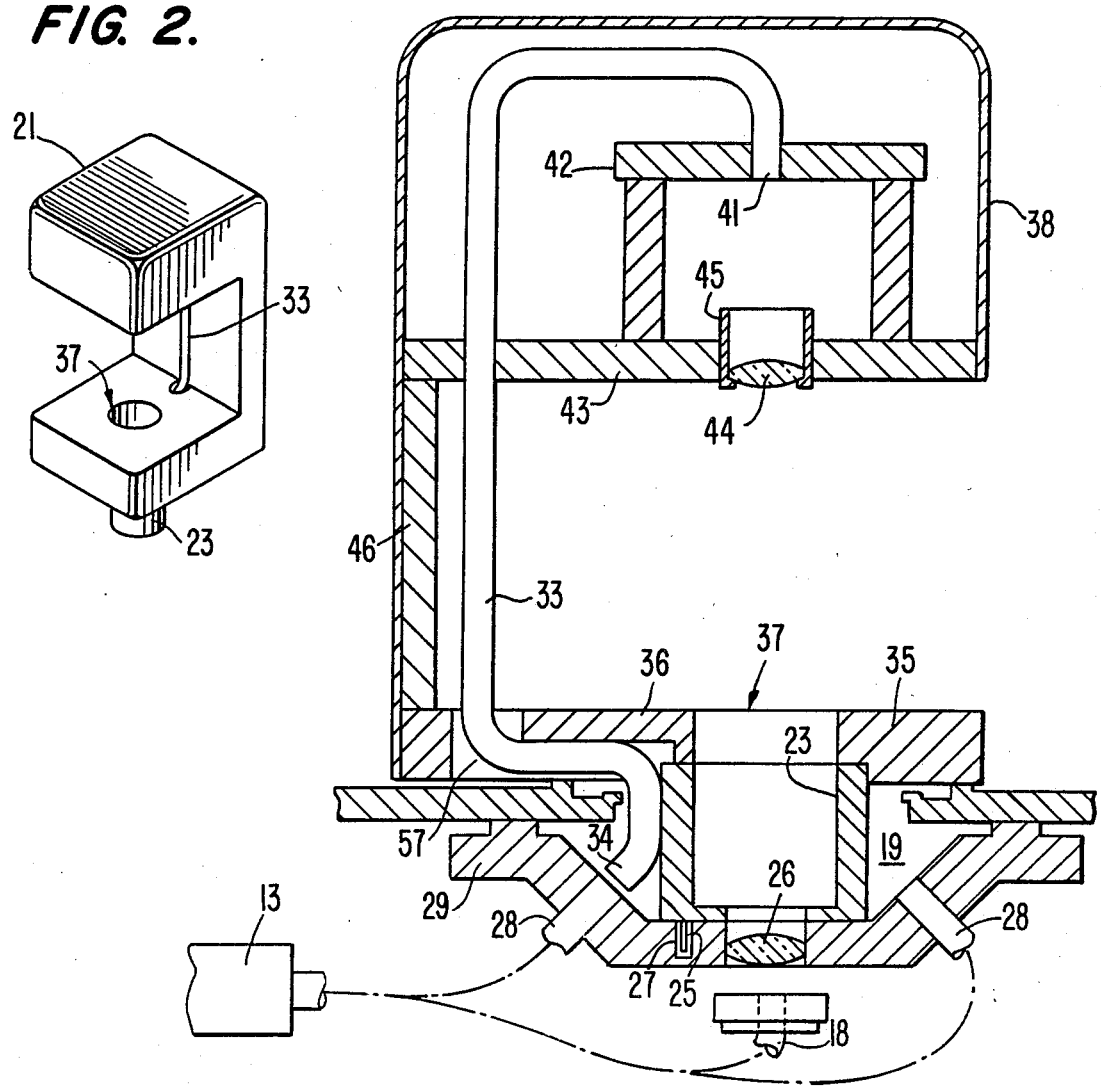
FIG. 2.
FIG. 3.

4,916,309

APPLIANCE FOR CONVERTING REFLECTANCE MEASURING INSTRUMENT INTO A TRANSMITTANCE MEASURING INSTRUMENT

BACKGROUND OF THE INVENTION

This invention relates to an accessory to be used with an optical instrument and, more particularly, to an appliance designed to convert a reflectance measuring instrument to a transmittance measuring instrument.

Optical instruments measuring color and also analyzing the constituents of a sample are typically designed to make measurements by the reflectance of light energy from the sample. In the case of some samples, it is desirable to use the same instruments to measure the transmittance through a sample. Prior to the present invention, appliances had been employed to convert reflectance measuring instruments into transmittance measuring instruments by housing a lamp in the appliance, which then directed a beam of light through a sample into the reflectance measuring instrument. The instrument analyzed the light transmitted through the sample with the same hardware employed to analyze reflected light from the sample. Because the lamp in the appliance generated heat, a fan was necessary also in the appliance to keep the appliance cool. However, even with the fan, the appliance tended to overheat. To supply power to the lamp and to the fan, a plug, a connecting cable and a power switch were required. In order to allow field installation of the accessory, the connecting hardware had to be built into every instrument whether or not the instrument employed the appliance. A major problem with the appliance was that the internal lamp in the base instrument used to make reflectance measurements ahd to be turned off so that light from this lamp could not interfere with the transmittance measurement. When the lamp in the base instrument was turned back on, further measurements had to be delayed to allow the instrument to warm up again before reflectance measurements could be made. Also, when the lamp in the appliance was turned on to perform a transmittance measurement, the appliance had to be allowed to warm up before it could be used.

SUMMARY OF THE INVENTION

The present invention overcomes the problems of the prior art appliance by making use of fiber optics. In accordance with the present invention, the appliance is made to fit with the aperture for receiving a reflectance sample. A fiber optic bundle in the appliance passes through the aperture and has a receiving end positioned to pick up light generated by the lamp employed to make reflectance measurements. The fiber optic bundle picks up the light at a point at which it is directed toward the aperture. The transmitting end of the fiber optic bundle is pointed toward the aperture and a lens directs the light emitted from the transmitted end of the fiber optic bundle through the sample, the transmittance of which is to be measured. The light, after passing through the transmittance sample, will enter the aperture of the instrument and is received and detected in the same manner as reflected light from a sample is received and detected. Since no lamp is used in the appliance, no overheating of the appliance occurs and no fan is required to keep the appliance cool. Since the lamp employed to generate the light transmitted through the sample is the same lamp that is used to make the reflectance measurements, the light does not need to be turned off and on to switch between reflectance and transmittance measurements and no waiting for warm up is required when such switching occurs.

BRIEF DESCRIPTION OF THE DRAWINGS

FIG. 1 schematically illustrates an optical instrument in combination with the appliance of the present invention to convert the instrument into a transmittance measuring instrument;

FIG. 2 is a perspective view of the appliance of the invention; and

FIG. 3 is a sectional view through the probe employed in the instrument of FIG. 1 with the appliance mounted on the probe of the instrument in position to convert the instrument into a transmittance measuring instrument.

DESCRIPTION OF THE PREFERRED EMBODIMENT

The reflectance measuring instrument for which the appliance is designed is described in copending application Ser. No. 868,700. As described in this application, and as shown in Fig. 1, the reflectance instrument comprises a probe 11 connected by a fiber optic cable 13 to a cabinet 14 containing a light source or lamp 15 and a spectrometer 17. Light from the lamp is received by a fiber optic bundle 16 in the cabinet 14 and transmitted via the cable 13 to the probe 11, in which the fiber optic bundle 16 is arranged to irradiate a sample placed over aperture 19 defined in the housing of the probe 11. When the instrument is being used to measure the reflectance of a sample, the sample is placed over the aperture 19 and light reflected from the sample is received by the receiving end of a fiber optic bundle 18 and carried back through the cable 13 to the cabinet 14, in which the bundle 18 transmits the light into the entrance slit of the spectrometer 17. The spectrometer 17 disperses the light into spectral components, the intensities of which are detected to measure the color of the sample. The instrument as described in the copending application also employs means to irradiate the sample with ultraviolet light to cause the sample to fluoresce and the spectral components of the fluorescence is also measured by the spectrometer 17. In the preferred embodiment of the appliance of this invention, the florescence measuring feature is not used and, accordingly, the ultraviolet light source and related hardware has been omitted from the illustration of FIG. 1 for the purposes of simplification.

In accordance with the present invention, an appliance 21 is provided to fit with and extend into the aperture 19, the appliance 21 being shown in Fig. 1 separated from the aperture 19 in position to be applied to the probe 11 over the aperture 19. The appliance 21 has a downwardly extending hollow projection 23 which extends into the aperture 19. Pins 25 mounted on the projection 23 and received in corresponding bores in the probe align the appliance in the correct orientation with respect to the probe.

As best shown in FIG. 3, the fiber optic bundle 16 which transmits light from the source 15 to the probe is divided into a plurality of transmitting ends 28 mounted in a fixture 29 and distributed around the aperture 19 to irradiate a sample positioned over the aperture from points surrounding the aperture. Light reflected from a sample positioned over the aperture is focused by lens 26 onto the receiving end of the fiber optic bundle 18, which carries the light reflected from the sample back to the spectrometer 17. The appliance 21 comprises a fiber optic bundle 33 which has a receiving end 34 positioned opposite one of the transmitting ends 28 which transmits light toward the aperture 19. When the appliance 21 is positioned in the aperture 19 as shown in FIG. 3, a lower platform 35 of the appliance 21 has a lower surface which rests on the top surface of the probe. The upper side of the platform 35 comprises a flat table surface 36 parallel to the plane of the aperture 19. The platform 35 has defined therein an aperture 37 coaxial with the aperture 19. The hollow tubular projection 23, which is mounted in the aperture 37 of the platform 35, has a lower surface which rests on a central flat annular surface of the fixture 29. The pins 25 fit in bores 27 formed in this flat annular surface. The transmittance sample to be measured is placed on the table surface 36 over the aperture 39. The fiber optic bundle 33 passes through the aperture 19 along side of the projection 23 and through a cavity 57 in the platform 35 and extends vertically into the upper housing 38 of the appliance where the transmitting end 41 of the fiber optic bundle 33 is mounted. A fixture 42 mounts the transmitting end 41 to be facing and coaxial with the apertures 37 and 19 and spaced above the aperture 37. The fixture 42 is mounted on an upper platform 43 comprising the floor of the upper housing 38. The upper platform 43 is cantilevered from a side plate 46, which in turn is mounted on the lower platform 35. A lens 44 is mounted in a lens holder 45 mounted in an aperture in the platform 43 positioned below the transmitting end 41 of the fiber optic bundle 33 but above the aperture 37 to leave room for different size samples to be placed on the table surface 36 over the aperture 37. The lens 44 colimates the light emitted from the transmitting end 41 of the bundle 33 and directs the collimated beam through the aperture 37 and the aperture 19 into the hollow projection 23 and into the probe 11. The collimated beam from the lens 44, after passing through a transmittance sample positioned over the aperture 37, will enter the projection 23 and be focused by the lens 26 onto the entrance end of the fiber optic bundle 18.

When the appliance 21 is in place in the aperture 19 with the pins 25 in the corresponding bores in the fixture 29, the entrance end 34 of the fiber optic bundle 33 will be aligned with one of the transmitting ends 28. Light from the source 15 will be carried in the fiber optic bundle 16 to the transmitting ends 28 mounted in the fixture 29. Light from all of the transmitting ends 28 but the one opposite the receiving end of the fiber optic bundle 33 will be blocked by the wall of the projection 23. Light emitted from the transmitting end 28 opposite the receiving end 34 of the fiber optic bundle 33 will be received by the fiber optic bundle 33 and carried to the transmitting end 41 where it will be emitted in a beam directed toward a sample over the aperture 39. The light after being collimated by the lens 44 will pass through the transmittance sample and then be focused by the lens 26 onto the receiving end of the fiber optic bundle 18, which will carry the received light back to the spectrometer 17 where the light will be dispersed into its spectral components and analyzed.

Since the fixture employs no lamp, it requires no fan to cool the fixture and is not subject to overheating. Also, the fixture requires no electrical power so no power cable or connections are required to energize components within the housing. The unit can be used on the existing instrument as disclosed in the copending application Ser. No. 868,700 referred to above.

While the instrument has been described as receiving light fron only one of the transmitting ends 28 of the fiber optic bundle 16, the bundle 33 could have its receiving ends divided into a plurality of separate receiving bundle ends to receive light from more than one of the transmitting ends 28 to increase the intensity of the light being transmitted through the sample placed over the opening 37. While the appliance has been described as specifically designed for the reflectance measuring instrument disclosed in application Ser. No. 868,700, it will be apparent that the appliance could be modified and adapted for application on other reflectance measuring instruments, such as, for example, the reflectance measuring instrument disclosed in the U.S. Pat. No. 4,464,054 to Philip Karras issued Aug. 7, 1984, and assigned to the assignee of this application. These and many other modifications may be made to the abovedescribed specific embodiment of the present invention without departing from the spirit and scope of the invention, which is defined in the appended claims.

I claim:

1. An appliance for converting a reflectance measuring instrument into a transmittance measuring instrument wherein said reflectance measuring instrument comprises reflectance sample receiving means to receive a reflectance sample, light sournce means to direct light toward a reflectance sample received by said reflectance sample receiving means to be reflected by such reflectance sample, and light receiving means to receive and perform measurements on light reflected by such reflectance sample, wherein said appliance comprises fitting means to make a fit with said instrument, means to receive a transmittance sample, fiber optic means having a receiving end positioned to receive light from said light source means when said fitting means makes a fit with said instrument, said fiber optic means having a transmitting end positioned to transmit light through a transmittance sample received by said transmittance sample receiving means to said light receiving means when said fitting means makes a fit with said instrument.

2. An appliance as recited in claim 1, wherein said reflectance sample receiving means comprises means defining an aperture to receive a reflectance sample over said aperture, said transmittance sample receiving means comprising means defining an aperture aligned with the aperture of said reflectance sample receiving means when said fitting means makes a fit with said instrument, said transmitting end of said fiber optic bundle being axially aligned with and pointed toward said first and second apertures.

3. An appliance as recited in claim 1, wherein said light source means comprises means to direct light from a plurality of different angular positions toward a reflectance sample received in said reflecting sample receiving means, said fiber optic bundle having its receiving end positioned to receive light from one of said angular positions when said fitting means makes a fit with said instrument, said appliance having means to block the light from the other ones of said angular positions from being transmitted to said transmittance sample receiving means when said fitting means makes a fit with said instrument.

4. An appliance as recited in claim 1, further comprising a collimating lens to collimate the light emitted from the transmitting end of said fiber optic bundle into a collimated beam directed toward said transmittance sample.

* * * * *